(12) United States Patent
Huang et al.

(10) Patent No.: US 12,161,508 B2
(45) Date of Patent: Dec. 10, 2024

(54) ULTRASONIC IMAGING METHOD AND DEVICE, AND STORAGE MEDIUM

(71) Applicant: BOE TECHNOLOGY GROUP CO., LTD., Beijing (CN)

(72) Inventors: Jijing Huang, Beijing (CN); Zhiming Yang, Beijing (CN); Zongmin Liu, Beijing (CN); Mengjun Hou, Beijing (CN); Dawei Tang, Beijing (CN); Qiong Wu, Beijing (CN)

(73) Assignee: Beijing BOE Technology Development Co., Ltd., Beijing (CN)

( * ) Notice: Subject to any disclaimer, the term of this patent is extended or adjusted under 35 U.S.C. 154(b) by 382 days.

(21) Appl. No.: 17/626,657

(22) PCT Filed: Mar. 11, 2021

(86) PCT No.: PCT/CN2021/080171
§ 371 (c)(1),
(2) Date: Jan. 12, 2022

(87) PCT Pub. No.: WO2021/180161
PCT Pub. Date: Sep. 16, 2021

(65) Prior Publication Data
US 2022/0287684 A1 Sep. 15, 2022

(30) Foreign Application Priority Data
Mar. 13, 2020 (CN) .......................... 202010177896.3

(51) Int. Cl.
*A61B 8/08* (2006.01)
*G01N 29/44* (2006.01)
*G01S 7/52* (2006.01)

(52) U.S. Cl.
CPC ........... *A61B 8/5207* (2013.01); *G01N 29/44* (2013.01); *G01S 7/52038* (2013.01); *G01S 7/52047* (2013.01)

(58) Field of Classification Search
None
See application file for complete search history.

(56) References Cited

U.S. PATENT DOCUMENTS 5,349,262 A * 9/1994 Grenon .................. G10K 11/32
310/334
5,551,433 A * 9/1996 Wright ................ G01S 7/52049
600/443
(Continued)

FOREIGN PATENT DOCUMENTS

CN 101940479 A * 1/2011
CN 108113703 A 6/2018
(Continued)

*Primary Examiner* — Isam A Alsomiri
*Assistant Examiner* — Jonathan D Armstrong
(74) *Attorney, Agent, or Firm* — HOUTTEMAN LAW LLC

(57) ABSTRACT

Provided are an ultrasonic imaging method and device, and a storage medium. The ultrasonic imaging method includes: acquiring an ultrasonic echo signal; segmenting the ultrasonic echo signal into a first predetermined number of sub-echo signals according to scan depths; performing amplitude apodization on each sub-echo signal with a predetermined window function to obtain processed sub-echo signals; completing ultrasonic imaging according to the processed sub-echo signals. At least one sub-echo signal is subjected to the follow processing: segmenting the at least one sub-echo signal into a second predetermined number of unit echo signals according to the scan depths, and assigning a weighting coefficient to each unit echo signal; performing amplitude apodization on each unit echo signal with the corresponding predetermined window function, and weight- (Continued)

ing the unit echo signals with corresponding weighting coefficients to obtain processed unit echo signals; and forming a processed sub-echo signal from the processed unit echo signals.

17 Claims, 3 Drawing Sheets

(56) References Cited

U.S. PATENT DOCUMENTS

| | | | | |
|---|---|---|---|---|
| 5,570,691 A * | 11/1996 | Wright | ................ | G10K 11/346 600/447 |
| 5,581,517 A * | 12/1996 | Gee | ................ | G01S 7/5209 367/138 |
| 5,590,658 A * | 1/1997 | Chiang | ................ | G01S 15/8979 600/447 |
| 5,675,554 A * | 10/1997 | Cole | ................ | G01S 7/52019 367/138 |
| 6,029,116 A * | 2/2000 | Wright | ................ | G01S 15/8988 702/32 |
| 2003/0007593 A1 * | 1/2003 | Heuscher | ................ | A61B 8/4416 378/4 |
| 2005/0237858 A1 * | 10/2005 | Thomenius | ................ | G01N 29/0609 367/155 |
| 2006/0094962 A1 * | 5/2006 | Clark | ................ | A61B 8/06 600/447 |
| 2009/0096327 A1 * | 4/2009 | Kristoffersen | ................ | G01S 15/8925 310/334 |
| 2009/0306512 A1 * | 12/2009 | Loftman | ................ | G01S 7/5209 600/447 |
| 2023/0213649 A1 * | 7/2023 | Ustuner | ................ | G01S 7/52047 600/447 |

FOREIGN PATENT DOCUMENTS

| | | |
|---|---|---|
| CN | 108836384 A | 11/2018 |
| CN | 111329517 A | 6/2020 |
| JP | 2018082835 A | 5/2018 |

* cited by examiner

ULTRASONIC IMAGING METHOD AND DEVICE, AND STORAGE MEDIUM

CROSS-REFERENCE TO RELATED APPLICATIONS

The present disclosure claims the priority to the Chinese Patent Application No. 202010177896.6 filed with the CNIPA on Mar. 13, 2020, the entire contents of which are incorporated herein by reference.

TECHNICAL FIELD

The present disclosure relates to the field of ultrasonic imaging technology, and in particular, to an ultrasonic imaging method, an ultrasonic imaging device, and a storage medium.

BACKGROUND

In a medical ultrasonic imaging system, the beam synthesis technology has been the hot technology in research for a long time, and the quality of the technology can directly affect final imaging quality. The beam synthesis technology includes the focusing technology, the amplitude apodization technology and the dynamic aperture technology.

The amplitude apodization technology is relative critical among the ultrasonic imaging technologies. However, when applied, a single amplitude apodization technique can obtain small side lobes only in a small range, and produce a poor ultrasonic imaging effect.

SUMMARY

In one aspect, the present disclosure provides an ultrasonic imaging method, including:
  acquiring an ultrasonic echo signal;
  segmenting the ultrasonic echo signal into a first predetermined number of sub-echo signals according to scan depths;
  performing amplitude apodization on each of the sub-echo signals with a predetermined window function to obtain processed sub-echo signals; and
  completing ultrasonic imaging according to the processed sub-echo signals.

At least one of the sub-echo signals is subjected to the follow processing:
  segmenting the at least one of the sub-echo signals into a second predetermined number of unit echo signals according to the scan depths, and assigning weighting coefficients to each of the unit echo signals;
  performing amplitude apodization on each of the unit echo signals with the predetermined window function corresponding to the at least one of the sub-echo signals, and weighting the unit echo signals with the weighting coefficients corresponding to the unit echo signals, so as to obtain processed unit echo signals; and
  forming the processed sub-echo signal from the second predetermined number of processed unit echo signals.

According to some implementations of the present disclosure, the method further includes: outputting an ultrasonic imaging result.

According to some implementations of the present disclosure, the first predetermined number is 4, 5 or 6.

According to some implementations of the present disclosure, segmenting the ultrasonic echo signal into the first predetermined number of sub-echo signals according to the scan depths includes:
  segmenting the ultrasonic echo signal into five sub-echo signals according to the scan depths, with scan depth ranges corresponding to the sub-echo signals being 0-2.5 cm, 2.5 cm-7.5 cm, 7.5 cm-12.5 cm, 12.5 cm-17.5 cm and 17.5 cm-20 cm respectively.

According to some implementations of the present disclosure, the predetermined window function includes at least one of a Blackman window function, a Hanning window function, a cosine window function and a rectangular window function.

According to some implementations of the present disclosure, the Blackman window function corresponds to the scan depth of 2.5 cm, the Hanning window function corresponds to the scan depth of 7.5 cm, the cosine window function corresponds to the scan depth of 12.5 cm, and the rectangular window function corresponds to the scan depth of 17.5 cm.

Performing amplitude apodization on each of the sub-echo signals with the predetermined window function includes:
  performing amplitude apodization on the sub-echo signal having the scan depth range of 0-2.5 cm with the Blackman window function;
  performing amplitude apodization on the sub-echo signal having the scan depth range of 2.5 cm-7.5 cm with the Blackman window function and the Hanning window function;
  performing amplitude apodization on the sub-echo signal having the scan depth range of 7.5 cm-12.5 cm with the Hanning window function and the cosine window function;
  performing amplitude apodization on the sub-echo signal having the scan depth range of 12.5 cm-17.5 cm with the cosine window function and the rectangular window function; and
  performing amplitude apodization on the sub-echo signal having the scan depth range of 17.5 cm-20 cm with the rectangular window function.

According to some implementations of the present disclosure, the second predetermined number is any integer from 8 to 12.

According to some implementations of the present disclosure, assigning the weighting coefficients to each of the unit echo signals includes: assigning two sets of weighting coefficients to the unit echo signals, with the two sets of weighting coefficients being a set of weighting coefficients in ascending order of value and a set of weighting coefficients in descending order of value respectively.

Performing amplitude apodization on each of the unit echo signals with the predetermined window function corresponding to the at least one of the sub-echo signals, and weighting the unit echo signals with the weighting coefficients corresponding to the unit echo signals to obtain the processed unit echo signals includes:
  performing amplitude apodization on each of the unit echo signals with two corresponding predetermined window functions to obtain two sets of processing results;
  weighting the two sets of processing results with the two sets of weighting coefficients respectively to obtain two sets of weighted processing results; and
  obtaining the processed unit echo signals according to the two sets of weighted processing results.

According to some implementations of the present disclosure, segmenting the at least one of the sub-echo signals into the second predetermined number of unit echo signals according to the scan depths includes: segmenting each of the least one of the sub-echo signal into 11 unit echo signals according to the scan depths. The sub-echo signal is a sub-echo signal corresponding to the scan depth range of 2.5 cm-7.5 cm, 7.5 cm-12.5 cm or 12.5 cm-17.5 cm, a difference between a maximum scan depth and a minimum scan depth of the scan depth range of each of the first unit echo signal and the last unit echo signal among the 11 unit echo signals is 0.25 cm, and the scan depth ranges of the second unit echo signal to the tenth unit echo signal among the 11 unit echo signals are divided at equal intervals of 0.5 cm.

The weighting coefficients in ascending order of value are integers from 0 to 10, and the weighting coefficients in descending order of value are integers from 10 to 0.

According to some implementations of the present disclosure, the method further includes:

performing amplitude apodization on the sub-echo signal having the scan depth range of 0-2.5 cm with the Blackman window function to obtain a processing result, and then multiplying the processing result by a weighting coefficient of 10; and performing amplitude apodization on the sub-echo signal having the scan depth range of 17.5 cm-20 cm with the rectangular window function to obtain a processing result, and then multiplying the processing result by a weighting coefficient of 10.

In another aspect, the present disclosure further provides an ultrasonic imaging device, including:

an acquisition unit configured to acquire an ultrasonic echo signal; and a processing unit configured to:

segment the ultrasonic echo signal into a first predetermined number of sub-echo signals according to scan depths;

perform amplitude apodization on each of the sub-echo signals with a predetermined window function to obtain processed sub-echo signals; and complete ultrasonic imaging according to the processed sub-echo signals.

The processing unit is further configured to:

segment at least one of the sub-echo signals into a second predetermined number of unit echo signals according to scan depths, and assign weighting coefficients to each of the unit echo signals;

perform amplitude apodization on each of the unit echo signals with the predetermined window function corresponding to the at least one of the sub-echo signals, and weight the unit echo signals with the weighting coefficients corresponding to the unit echo signals to obtain processed unit echo signals; and form the processed sub-echo signal from the second predetermined number of processed unit echo signals.

According to some implementations of the present disclosure, the ultrasonic imaging device further includes: an output unit configured to output an ultrasonic imaging result.

According to some implementations of the present disclosure, the processing unit is further configured to:

segment the ultrasonic echo signal into five sub-echo signals according to the scan depths, with scan depth ranges corresponding to the sub-echo signals being 0-2.5 cm, 2.5 cm-7.5 cm, 7.5 cm-12.5 cm, 12.5 cm-17.5 cm and 17.5 cm-20 cm respectively.

According to some implementations of the present disclosure, the predetermined window function includes at least one of a Blackman window function, a Hanning window function, a cosine window function and a rectangular window function.

According to some implementations of the present disclosure, the Blackman window function corresponds to the scan depth of 2.5 cm, the Hanning window function corresponds to the scan depth of 7.5 cm, the cosine window function corresponds to the scan depth of 12.5 cm, and the rectangular window function corresponds to the scan depth of 17.5 cm; and the processing unit is further configured to:

perform amplitude apodization on the sub-echo signal having the scan depth range of 0-2.5 cm with the Blackman window function;

perform amplitude apodization on the sub-echo signal having the scan depth range of 2.5 cm-7.5 cm with the Blackman window function and the Hanning window function;

perform amplitude apodization on the sub-echo signal having the scan depth range of 7.5 cm-12.5 cm with the Hanning window function and the cosine window function;

perform amplitude apodization on the sub-echo signal having the scan depth range of 12.5 cm-17.5 cm with the cosine window function and the rectangular window function; and perform amplitude apodization on the sub-echo signal having the scan depth range of 17.5 cm-20 cm with the rectangular window function.

According to some implementations of the present disclosure, the processing unit is further configured to:

assign two sets of weighting coefficients to the unit echo signals, with the two sets of weighting coefficients being a set of weighting coefficients in ascending order of value and a set of weighting coefficients in descending order of value respectively;

perform amplitude apodization on each of the unit echo signals with two corresponding predetermined window functions to obtain two sets of processing results;

weight the two sets of processing results with the two sets of weighting coefficients respectively to obtain two sets of weighted processing results; and obtain the processed unit echo signal according to the two sets of weighted processing results.

According to some implementations of the present disclosure, the processing unit is further configured to:

segment each of the at least one of the sub-echo signals into 11 unit echo signals according to the scan depths. The sub-echo signal is the sub-echo signal corresponding to the scan depth range of 2.5 cm-7.5 cm, 7.5 cm-12.5 cm or 12.5 cm-17.5 cm, a difference between a maximum scan depth and a minimum scan depth of the scan depth range of each of the first unit echo signal and the last unit echo signal among the 11 unit echo signals is 0.25 cm, and the scan depth ranges of the second unit echo signal to the tenth unit echo signal among the 11 unit echo signals are divided at equal intervals of 0.5 cm.

The weighting coefficients in ascending order of value are integers from 0 to 10, and the weighting coefficients in descending order of value are integers from 10 to 0.

According to some implementations of the present disclosure, the processing unit is further configured to:

perform amplitude apodization on the sub-echo signal having the scan depth range of 0-2.5 cm with the Blackman window function to obtain a processing result, and then multiply the processing result by a weighting coefficient of 10; and perform amplitude apodization on the sub-echo signal having the scan depth range of 17.5 cm-20 cm with the rectangular window function to obtain a processing result, and then multiply the processing result by a weighting coefficient of 10.

In another aspect, the present disclosure further provides a non-transitory computer-readable storage medium having computer instructions stored therein. When The computer instructions causes, when executed by a processor, a computer to perform the method described herein accordingly.

BRIEF DESCRIPTION OF DRAWINGS

In order to describe one or more embodiments of the present disclosure or the technical solutions in the related art more clearly, the drawings for the description of the embodiments or the related art will be simply described below. It should be understood that the drawings described below are merely for one or more embodiments of the present disclosure, and other drawings can be derived from the described drawings by those of ordinary skill in the art without creative labor.

DETAIL DESCRIPTION OF EMBODIMENTS

Figure 1:
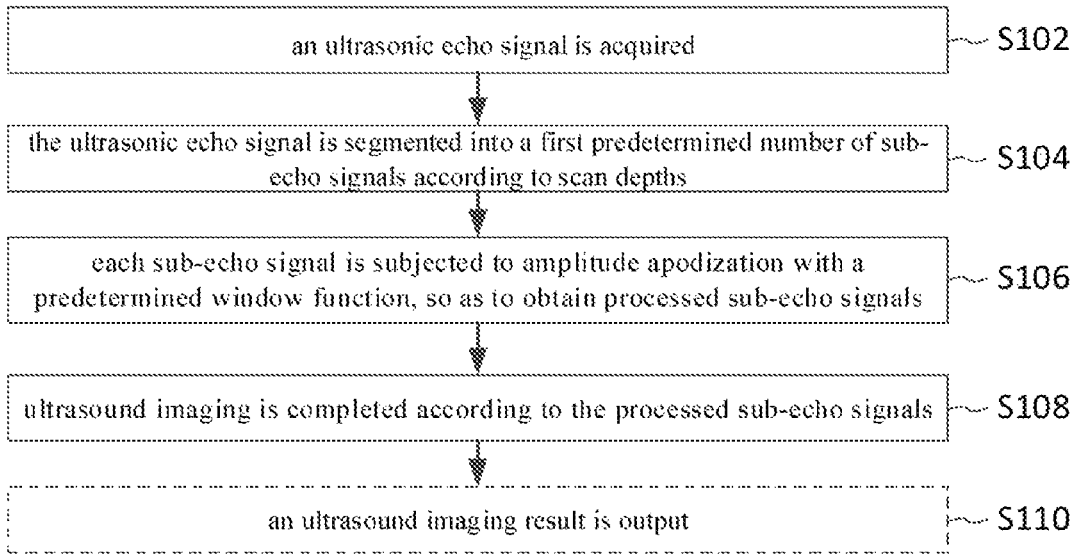
FIG. 1 is a flowchart illustrating an ultrasonic imaging method according to one or more embodiments of the present disclosure.

In order to make the objectives, technical solutions and advantages of the present disclosure clearer, the present disclosure is further described in detail below in conjunction with the specific embodiments and the drawings.

It should be noted that, unless otherwise defined, technical terms or scientific terms used in the one or more embodiments of the present disclosure should have general meanings that are understood by those of ordinary skills in the technical field of the present disclosure. The words "first", "second" and the like (if any) used in the one or more embodiments of the present disclosure do not denote any order, quantity or importance, but are just used to distinguish between different elements. The words "include", "comprise" and the like indicate that an element or object before the words covers the elements or objects or the equivalents thereof listed after the words, rather than excluding other elements or objects. The words "connect", "couple" and the like are not restricted to physical or mechanical connection, but may also indicate electrical connection, whether direct or indirect. The words "on", "under", "left", "right" and the like are only used to indicate relative positional relationships. When an absolute position of an object described is changed, the relative positional relationships may also be changed accordingly.

In the Description, the reference terms such as "one embodiment", "some embodiments", "an example", "a specific example" and "some examples" indicate that the specific features, structures, materials or characteristics described in the embodiment(s) or example(s) are included in at least one embodiment or example of the present disclosure. In the Description, the illustrative descriptions of the above terms are not necessarily for the same embodiment or example. Moreover, the specific features, structures, materials or characteristics described may be combined in any suitable way in any one or more embodiments or examples. Furthermore, the embodiments of the present disclosure and the features therein may be combined with each other if no conflict is incurred.

Amplitude apodization refers to adding an amplitude coefficient to an echo signal of each array element. If the signals collected by different array elements are simply added with equal amplitude during delay-and-sum beamforming, side lobes of the ultrasonic echoes are large, which leads to an increase of artifacts in final ultrasonic imaging and a decrease in image contrast. In order to reduce a width of a main lobe and suppress the amplitude of a side lobe, a method is adopted to multiply echo signals collected by different array elements of an ultrasonic probe by different coefficients according to a contribution of each echo signal to the amplitude of a focus, and then add the echo signals together. Such processing method is called amplitude apodization. The principle of performing amplitude apodization is: for an array element with a large contribution to the focus, the echo signal collected by the array element is multiplied by a larger coefficient to obtain a new value, and then the original value is replaced with the new value for superposition; and for an array element with a small contribution to the focus, the echo signal collected by the array element is multiplied by a smaller coefficient to obtain a new value, and then the original value is replaced with the new value for superposition. It is generally believed that an array element at a central position in the probe has the largest contribution to the focus, and an array element at the outermost position has the least contribution to the focus. Amplitude apodization can be implemented in many ways, and window functions are most commonly used.

An amplitude apodization technique adopts segmental dynamic apodization, which has high flexibility in function design and can be implemented in various ways. The segmental dynamic apodization has an advantage that small side lobes can be obtained in all detection depths, but also has the disadvantages that the function design is complex, and what is usually obtained is an apodization coefficient of the focus, which needs a large number of segments and causes complicated calculation.

In addition, when dynamic amplitude apodization adopts the segmental dynamic apodization, in the case of a large number of segments, more resources are occupied, but the ultrasonic imaging quality is better; and in the case of a small number of segments, fewer resources are occupied, but the ultrasonic imaging quality is poor.

According to an ultrasonic imaging method and device and a storage medium provided in one or more embodiments of the present disclosure, an ultrasonic echo signal is segmented into several sub-echo signals, at least one of the sub-echo signals is selected to be further segmented to obtain several unit echo signals, each of the several sub-echo signals is then subjected to amplitude apodization with a predetermined window function (the several unit echo signals are subjected to amplitude apodization with the predetermined window function and then are weighted with weighting coefficients), and finally ultrasonic imaging is completed according to processed sub-echo signals. According to the present disclosure, on the basis of performing amplitude apodization with the window function, at least one of the sub-echo signals is segmented to several unit echo signals, which are subjected to amplitude apodization with the predetermined window function and then are weighted with weighting coefficients, so that the unit echo signals are smoother, and a better ultrasonic imaging effect can be produced after the amplitude apodization.

FIG. 1 is a flowchart illustrating an ultrasonic imaging method according to one or more embodiments of the present disclosure. As shown in FIG. 1, the ultrasonic imaging method according to one or more embodiments of the present disclosure may include steps S102, S104, S106, S108 and S110.

At the step S102, an ultrasonic echo signal is acquired. The ultrasonic echo signal may be collected by an ultrasound device. In some implementations, the ultrasound device includes a transmitter and a receiver. In some implementations, the transmitter is an 8-element transmitter and the receiver is an 8-element receiver. In some implementations, both the transmitter and the receiver may adopt a dedicated ultrasound chip.

At the step S104, the ultrasonic echo signal is segmented into a first predetermined number of sub-echo signals according to scan depths. In some implementations, the first predetermined number is 4, 5 or 6, the ultrasonic echo signal is segmented into 4 to 6 sub-echo signals according to the scan depths, and amplitude apodization is performed subsequently. Thus, on the one hand, the final ultrasonic imaging quality may be ensured; on the other hand, fewer resources are occupied, so that a balance between the ultrasonic imaging quality and the resource occupation may be struck.

In an embodiment, the first predetermined number may be 5, and the ultrasonic echo signal may be segmented into five sub-echo signals according to the scan depths. For example, the scan depth ranges corresponding to the sub-echo signals may be 0 cm-2.5 cm, 2.5 cm -7.5 cm, 7.5 cm -12.5 cm, 12.5 cm -17.5 cm and 17.5 cm -20 cm.

At the step S106, each sub-echo signal is subjected to amplitude apodization with a predetermined window function, so as to obtain processed sub-echo signals.

In ultrasonic imaging, an effect of a beam formed by receiving the echo signal in a delay-and-sum manner is as follows:

$$s_{DAS}(t) = \sum_{n=0}^{N-1} s\left(t - \frac{r}{c} - \tau_n\right).$$

After the amplitude apodization is introduced, the above equation becomes:

$$s_{DAS}(t) = \sum_{n=0}^{N-1} w_n s\left(t - \frac{r}{c} - \tau_n\right).$$

Where s(t) is a received ultrasonic echo signal; N is a total number of array elements; r/c is the time for an ultrasonic signal of a linear array to propagate from a point p (x, y) in space to the coordinate origin; $\tau_n$ is a focusing delay applied to an array element n; and $W_n$ is an amplitude apodization function coefficient.

Functions used in amplitude apodization are usually window functions. The window function is a signal with a limited width in time domain, and different window functions may be used in a time domain to truncate/divide a signal.

In some implementations, the predetermined window function includes a Blackman window function, a Hanning window function, a cosine window function and/or a rectangular window function.

Specifically, the Blackman window function is:

$$w_n = 0.42 - 0.5\cos\left[\frac{2\pi n}{N-1}\right] + 0.08\cos\left[\frac{4\pi n}{N-1}\right]$$

The Hanning window function is:

$$w_n = 0.5 - 0.5\cos\left[\frac{2\pi n}{N-1}\right]$$

The cosine window function is:

$$w_n = \cos\left[\frac{\pi n}{N-1}\right]$$

The rectangular window function is: $w_n=1$.

Where n=0, . . . N−1, and N is the total number of the array elements.

In an implementation, for example, the scan depth ranges corresponding to the sub-echo signals may be 0 cm-2.5 cm, 2.5 cm-7.5 cm, 7.5 cm-12.5 cm, 12.5 cm-17.5 cm and 17.5 cm-20 cm, the Blackman window function may correspond to the scan depth of 2.5 cm, the Hanning window function may correspond to the scan depth of 7.5 cm, the cosine window function may correspond to the scan depth of 12.5 cm, and the rectangular window function may correspond to the scan depth of 17.5 cm. Therefore, by use of the characteristics of the different window functions, the sub-echo signal with the scan depth corresponding to each window function may achieve better resolution during the amplitude apodization.

In an implementation, performing amplitude apodization on each sub-echo signal with a predetermined window function includes:

performing amplitude apodization on the sub-echo signal corresponding to the scan depth range of 0 cm-2.5 cm with the Blackman window function;

performing amplitude apodization on the sub-echo signal corresponding to the scan depth range of 2.5 cm-7.5 cm with the Blackman window function and the Hanning window function;

performing amplitude apodization on the sub-echo signal corresponding to the scan depth range of 7.5 cm-12.5 cm with the Hanning window function and the cosine window function; and performing amplitude apodization on the sub-echo signal corresponding to the scan depth range of 12.5 cm-17.5 cm with the cosine window function and the rectangular window function.

performing amplitude apodization on the sub-echo signal corresponding to the scan depth range of 17.5 cm-20 cm with the rectangular window function.

Thus, with the different window functions used for the corresponding sub-echo signals according to the characteristics of the window functions, the image resolution can be better improved.

It should be noted that different window functions or combinations of window functions are used to perform amplitude apodization on the sub-echo signals in the above embodiments, but the embodiments are merely for illustration. It should be understood that the selection of the window functions and the scan depths corresponding to the window functions can be changed according to different scenes and different requirements.

In addition, the above way of segmenting the ultrasonic echo signal is also for illustration, and the number of segments and the scan depth ranges selected for the segmentation can be adjusted according to different scenes and different requirements.

At the step S108, ultrasonic imaging is completed according to the processed sub-echo signals. In some implementations, in this step, after the sub-echo signals are processed, all the sub-echo signals are formed into a whole ultrasonic echo signal which has already been processed through amplitude apodization, and then a subsequent imaging operation is performed to complete the ultrasonic imaging, that is, the ultrasonic echo signals are converted into ultrasonic image data. The ultrasonic imaging may be performed according to the ultrasonic echo signals with an existing method which is not limited herein.

Figure 2:
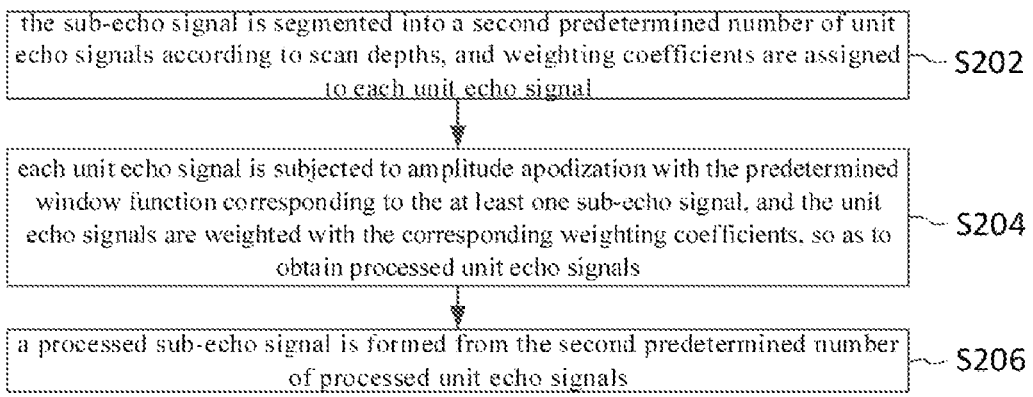
FIG. 2 is a flowchart of processing of sub-echo signals in the ultrasonic imaging method according to one or more embodiments of the present disclosure.

FIG. 2 is a flowchart of processing of sub-echo signals in the ultrasonic imaging method according to one or more embodiments of the present disclosure. As shown in FIG. 2, In some implementations, at least one of the sub-echo signals may be processed through the following steps S202, S204 and S206.

At the step S202, the sub-echo signal is segmented into a second predetermined number of unit echo signals according to scan depths, and weighting coefficients are assigned to each unit echo signal.

In some implementations, the second predetermined number may be any integer from 8 to 12, the sub-echo signal may be segmented into 8 to 12 unit echo signals according to the scan depths, the unit echo signals are assigned with their respective weighting coefficients, and then subsequent amplitude apodization and weighting are performed, so that the processed echo signals finally obtained may be smoother, and a better imaging effect may be produced.

In an embodiment, two sets of weighting coefficients may be assigned to the unit echo signals, and the two sets of weighting coefficients may be a set of weighting coefficients in ascending order of value and a set of weighting coefficients in descending order of value, respectively. Thus, processing results of amplitude apodization of the unit echo signals are weighted with the weighting coefficients in ascending or descending order of value, so that the processing results may be smoother, and a better imaging effect may be produced.

In an embodiment, segmenting the sub-echo signal into the second predetermined number of unit echo signals according to the scan depths may include: segmenting the sub-echo signal into 11 unit echo signals according to the scan depths. The sub-echo signal is the sub-echo signal corresponding to the scan depth range of 2.5 cm-7.5 cm, 7.5 cm-12.5 cm or 12.5 cm-17.5 cm, a difference between a maximum scan depth and a minimum scan depth of the scan depth range of each of the first unit echo signal and the last unit echo signal among the 11 unit echo signals is 0.25 cm, and each of the scan depth ranges of the other 9 unit echo signals (i.e., the second unit echo signal to the tenth unit echo signal) among the 11 unit echo signals has a span of 0.5 cm, that is, a difference between a maximum scan depth and a minimum scan depth of the scan depth range of each of the second unit echo signal to the tenth unit echo signal is 0.5 cm.

For example, taking the sub-echo signal with the scan depth range of 2.5 cm-7.5 cm as an example, the scan depth ranges corresponding to the first unit echo signal and the last unit echo signal are 2.5 cm-2.75 cm and 7.25 cm-7.5 cm, respectively; and the scan depth ranges corresponding to the other 9 unit echo signals are 2.75 cm-3.25 cm, 3.25 cm-3.75 cm, 3.75 cm-4.25 cm, 4.25 cm-4.75 cm, 4.75 cm-5.25 cm, 5.25 cm-5.75 cm, 5.75 cm-6.25 cm, 6.25 cm-6.75 cm and 6.75 cm-7.25 cm, respectively. In an embodiment, the weighting coefficients in ascending order of value may be integers from 0 to 10, and the weighting coefficients in descending order of value may be integers from 10 to 0.

In this way, the sub-echo signal are segmented into 11 segments which may just correspond to the above setting of the weighting coefficients, so that each segment can correspond to a set of weighting coefficients, which may facilitate smoother segmental amplitude apodization, thereby producing a better imaging effect.

At the step S204, each unit echo signal is subjected to amplitude apodization with the predetermined window function corresponding to the at least one sub-echo signal, and the unit echo signals are weighted with the corresponding weighting coefficients, so as to obtain processed unit echo signals.

Figure 3:
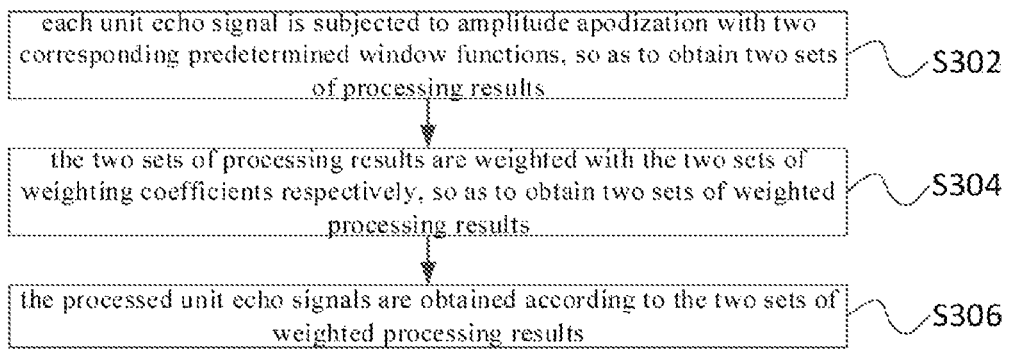
FIG. 3 is a flowchart of processing of unit echo signals in the ultrasonic imaging method according to one or more embodiments of the present disclosure.

FIG. 3 is a flowchart of processing of unit echo signals in the ultrasonic imaging method according to one or more embodiments of the present disclosure. As shown in FIG. 3, In some implementations, the step S204 may further include the following steps S302, S304 and S306.

At the step S302, each unit echo signal is subjected to amplitude apodization with two corresponding predetermined window functions, so as to obtain two sets of processing results.

For example, taking the sub-echo signal with the scan depth range of 2.5 cm-7.5 cm as an example, each unit echo signal may be subjected to amplitude apodization with the Blackman window function and the Hanning window function, so as to obtain a set of processing results based on the Blackman window function and a set of processing results based on the Hanning window function.

At the step S304, the two sets of processing results are weighted with the two sets of weighting coefficients respectively, so as to obtain two sets of weighted processing results.

For example, taking a case where the weighting coefficients in ascending order of value are integers from 0 to 10 respectively and the weighting coefficients in descending order of value are integers from 10 to 0 respectively as an example, assuming that the two sets of processing results are the processing results of the sub-echo signal with the scan depth range of 2.5 cm-7.5 cm, the set of processing results based on the Blackman window function may be weighted with the integers from 10 to 0, and the set of processing results based on the Hanning window function may be weighted with the integers from 0 to 10.

Specifically, after the unit echo signals with the scan depth ranges of 2.5 cm-2.75 cm, 2.75 cm-3.25 cm, 3.25 cm-3.75 cm, 3.75 cm-4.25 cm, 4.25 cm-4.75 cm, 4.75 cm-5.25 cm, 5.25 cm-5.75 cm, 5.75 cm-6.25 cm, 6.25 cm-6.75 cm, 6.75 cm-7.25 cm and 7.25 cm-7.5 cm are subjected to amplitude apodization with the Blackman window function, the processing result of the unit echo signal with the scan depth range of 2.5 cm-2.75 cm is multiplied by 10, the processing result of the unit echo signal with the scan depth range of 2.75 cm-3.25 cm is multiplied by 9, and so on, and the processing result of the unit echo signal with the scan depth range of 7.25 cm-7.5 cm is multiplied by 0 (or the processing result of such unit echo signal is directly discarded).

Similarly, after the unit echo signals with the scan depth ranges of 2.5 cm-2.75 cm, 2.75 cm-3.25 cm, 3.25 cm-3.75 cm, 3.75 cm-4.25 cm, 4.25 cm-4.75 cm, 4.75 cm-5.25 cm, 5.25 cm-5.75 cm, 5.75 cm-6.25 cm, 6.25 cm-6.75 cm, 6.75 cm-7.25 cm and 7.25 cm-7.5 cm are subjected to amplitude apodization with the Hanning window function, the processing result of the unit echo signal with the scan depth range of 2.5 cm-2.75 cm is multiplied by 0 (or the processing result of such unit echo signal is directly discarded), the processing result of the unit echo signal with the scan depth range of 2.75 cm-3.25 cm is multiplied by 1, and so on, and the processing result of the unit echo signal with the scan depth range of 7.25 cm-7.5 cm is multiplied by 10.

At the step S306, the processed unit echo signals are obtained according to the two sets of weighted processing results.

Thus, with the echo signal processed through segmentation and weighting, a smoother signal can be obtained, and a better final imaging effect can be produced.

With reference to FIG. 2 again, at the step S206, a processed sub-echo signal is formed from the second predetermined number of processed unit echo signals.

In some implementations, the ultrasonic imaging method may further include:

performing amplitude apodization on the sub-echo signal corresponding to the scan depth range of 0-2.5 cm with the Blackman window function to obtain a processing result, and then multiplying the processing result by a weighting coefficient of 10; and performing amplitude apodization on the sub-echo signal corresponding to the scan depth range of 17.5 cm-20 cm with the rectangular window function to obtain a processing result, and then multiplying the processing result by a weighting coefficient of 10.

It should be noted that, in a case where the sub-echo signals corresponding to the scan depth ranges of 2.5 cm-7.5 cm, 7.5 cm-12.5 cm and 12.5 cm-17.5 cm are subjected to weighting, the sub-echo signals corresponding to the scan depth ranges of 0-2.5 cm and 17.5 cm-20 cm are also multiplied by the weighting coefficient of 10 to maintain consistency of data size.

It should be understood that the step S206 can also be implemented through normalization, and a specific normalization process may be found in existing normalization methods, and thus is not described herein.

In some implementations, the sub-echo signals corresponding to different scan depths may be sequentially subjected to amplitude apodization. For example, in a case where ultrasound scanning is performed from shallow to deep, when an ultrasonic echo signal with a relative small scan depth is collected, sub-echo signals with a small scan depth may be subjected to amplitude apodization first; as the scan depth increases, sub-echo signals with larger scan depths are subjected to amplitude apodization sequentially according to the scan depths. The processing steps may be implemented with other processing methods which are not limited herein.

With reference to FIG. 1 again, the ultrasonic imaging method further includes step S110.

At the step S110, an ultrasonic imaging result is output. In this step, the ultrasonic imaging result is output, that is, ultrasonic image data obtained by ultrasonic imaging is output, so that a user may observe and analyze an ultrasonic image.

In some implementations, the ultrasonic imaging result may be output in any way. In an example, the ultrasonic imaging result may be displayed by a display device, so as to be output. In another example, the ultrasonic imaging result may be printed to be output. Thus, the processing result may be visualized as an ultrasonic image, which improves the user's experience.

In some implementations, the ultrasonic imaging result may be sent to a designated terminal, such as a work computer of an attending doctor and a mobile phone of a patient.

According to the ultrasonic imaging method provided in one or more embodiments of the present disclosure, an ultrasonic echo signal is segmented into several sub-echo signals, at least one of the sub-echo signals is selected to be further segmented to obtain several unit echo signals, each of the several sub-echo signals is then subjected to amplitude apodization with a predetermined window function (the several unit echo signals are subjected to amplitude apodization with the predetermined window function and then are weighted with weighting coefficients), and finally ultrasonic imaging is completed according to processed sub-echo signals. According to the technical solutions, on the basis of performing amplitude apodization with the window function, at least one of the sub-echo signals is segmented into several unit echo signals, which are subjected to amplitude apodization with the predetermined window function and then are weighted with weighting coefficients, so that the unit echo signals are smoother, and a better ultrasonic imaging effect can be produced after the amplitude apodization.

It should be noted that the method provided in one or more embodiments of the present disclosure may be performed by a single device, such as a computer or a server. The method provided in the present disclosure can also be applied to a distributed scenario and implemented through cooperation of a plurality of devices. In the distributed scenario, one of the plurality of devices may just perform one or more steps of the method provided in one or more embodiments of the present disclosure, and the plurality of devices can interact with one another to complete the method.

Figure 4:
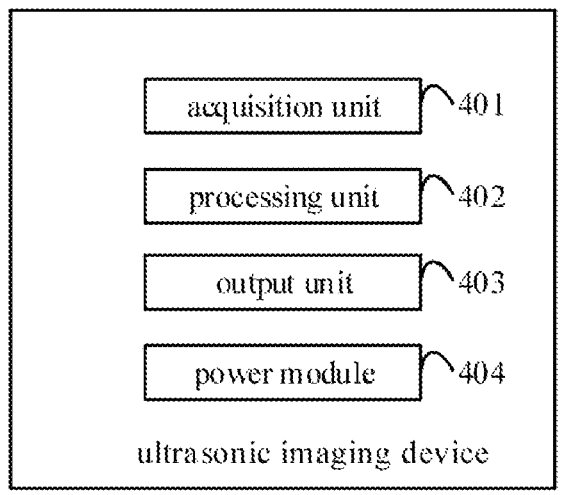
FIG. 4 is a schematic structural diagram of an ultrasonic imaging device according to one or more embodiments of the present disclosure.

FIG. 4 is a schematic structural diagram of an ultrasonic imaging device according to one or more embodiments of the present disclosure. As shown in FIG. 4, In some implementations, the ultrasonic imaging device includes:

an acquisition unit 401 configured to acquire an ultrasonic echo signal; and a processing unit 402 configured to:

segment the ultrasonic echo signal into a first predetermined number of sub-echo signals according to scan depths;

perform amplitude apodization on each of the sub-echo signals with a predetermined window function to obtain processed sub-echo signals; and complete ultrasonic imaging according to the processed sub-echo signals.

The processing unit 402 is further configured to:

segment the sub-echo signal into a second predetermined number of unit echo signals according to scan depths, and assign weighting coefficients to the unit echo signals;

perform amplitude apodization on each unit echo signal with the predetermined window function corresponding to the at least one sub-echo signal, and weight the unit echo signals with the weighting coefficients corresponding to the unit echo signals to obtain processed unit echo signals; and form the processed sub-echo signal from the second predetermined number of processed unit echo signals.

According to the ultrasonic imaging device provided in one or more embodiments of the present disclosure, an ultrasonic echo signal is segmented into several sub-echo signals, at least one of the sub-echo signals is selected to be further segmented to obtain several unit echo signals, each of the several sub-echo signals is then subjected to amplitude apodization with a predetermined window function (the several unit echo signals are subjected to amplitude apodization with the predetermined window function and then are weighted with weighting coefficients), and finally ultrasonic imaging is completed according to processed sub-echo signals. According to the technical solutions, on the basis of performing amplitude apodization with the window function, at least one of the sub-echo signals is segmented into several unit echo signals, which are subjected to amplitude apodization with the predetermined window function and then are weighted with weighting coefficients, so that the unit echo signals are smoother, and a better ultrasonic imaging effect can be produced after the amplitude apodization.

In some implementations, the acquisition unit 401 may include an ultrasonic receiving chip configured to receive ultrasonic echo signals collected by an ultrasonic probe. In an example, the ultrasonic receiving chip may send the signals to the processing unit 402 after amplifying the signals. The processing unit 402 may be implemented by a Field Programmable Gate Array (FPGA).

In an implementation, the FPGA is mainly configured to control an ultrasonic transmitting chip and the ultrasonic receiving chip, and process the received ultrasonic echo signals by algorithms, which include beam synthesis, dynamic filtering, envelope detection and logarithmic compression, and the beam synthesis includes dynamic focusing, amplitude apodization and dynamic aperture.

In an implementation, a Read-Only Memory (ROM) of the FPGA may further store a discretization coefficient of each window function and a corresponding weighting coefficient. After data reception is started, the FPGA may calculate a current scan depth according to the arrival time of data, determine a position corresponding to the current data (i.e., a position corresponding to the scan depth), and read the coefficient of a corresponding window function and the corresponding weighting coefficient from the ROM to perform corresponding calculations.

In an implementation, the data processing steps of the ultrasonic imaging method are performed inside the FPGA.

Figure 5:
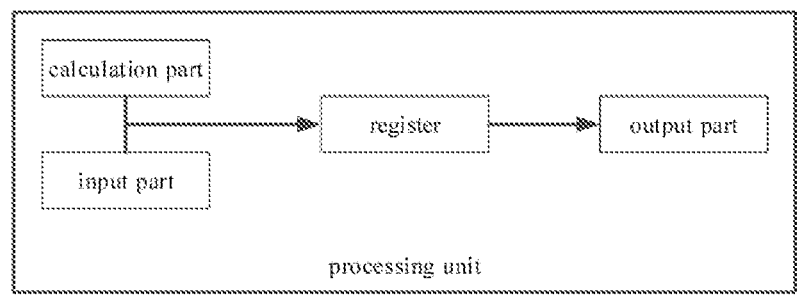
FIG. 5 is a schematic structural diagram of a processing unit according to one or more embodiments of the present disclosure.

FIG. 5 is a schematic structural diagram of a processing unit according to one or more embodiments of the present disclosure. As shown in FIG. 5, In some implementations, a processing unit includes: a calculation part configured to control timing of an entire program; a register configured to store different window function coefficients; an input part configured to input data (e.g., 8-way data) from the ultrasonic receiving chip to the FPGA; and an output part configured to output data obtained after beam synthesis of different data weighted with the different window function coefficients. In an implementation, the FPGA may further include a multiplier and a display look-up table (LUT), which are needed in the calculations.

In an implementation, the ultrasonic imaging device may further include a power module 404 configured to supply power to the ultrasonic imaging device.

Figure 6:
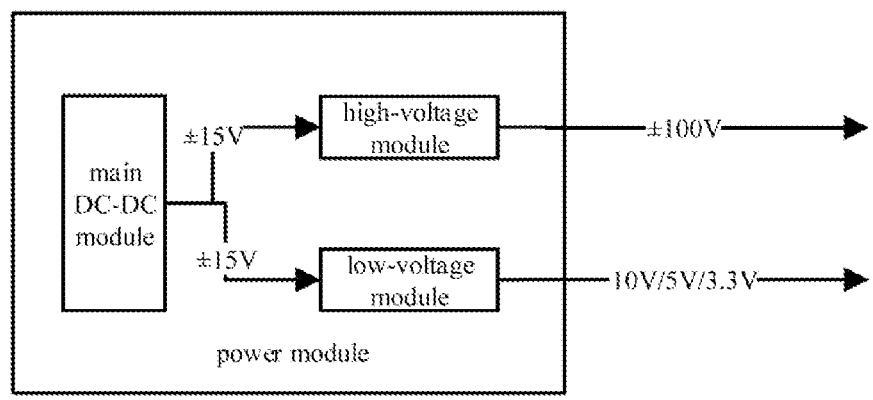
FIG. 6 is a schematic structural diagram of a power module according to one or more embodiments of the present disclosure.

FIG. 6 is a schematic structural diagram of a power module according to one or more embodiments of the present disclosure. As shown in FIG. 6, In some implementations, a power module may include a main DC-DC module, a high-voltage module and a low-voltage module. The DC-DC module generates a voltage of ±15V for the following modules, the high-voltage module generates a voltage of ±100V for an ultrasonic transmitting integrated circuit, and the low-voltage module generates common voltages of 10V, 5V, 3.3V and the like for the following circuits.

With reference to FIG. 4 again, In some implementations, the ultrasonic imaging device may further include an output unit 403 configured to output an ultrasonic imaging result. The output unit 403 may include a display device, and upper computer software mainly configured to receive calculated echo data for the display device to display.

In some implementations, the first predetermined number may be 4, 5 or 6.

In some implementations, the processing unit 402 may be configured to: segment the ultrasonic echo signal into five sub-echo signals according to scan depths, with scan depth ranges corresponding to the sub-echo signals being 0-2.5 cm, 2.5 cm-7.5 cm, 7.5 cm-12.5 cm, 12.5 cm-17.5 cm and 17.5 cm-20 cm respectively.

In some implementations, the predetermined window function includes a Blackman window function, a Hanning window function, a cosine window function and/or a rectangular window function.

In some implementations, the Blackman window function may correspond to the scan depth of 2.5 cm, the Hanning window function may correspond to the scan depth of 7.5 cm, the cosine window function may correspond to the scan depth of 12.5 cm, and the rectangular window function may correspond to the scan depth of 17.5 cm.

In some implementations, the processing unit 402 may be configured to:
perform amplitude apodization on the sub-echo signal corresponding to the scan depth range of 0-2.5 cm with the Blackman window function;
perform amplitude apodization on the sub-echo signal corresponding to the scan depth range of 2.5 cm-7.5 cm with the Blackman window function and the Hanning window function;
perform amplitude apodization on the sub-echo signal corresponding to the scan depth range of 7.5 cm-12.5 cm with the Hanning window function and the cosine window function;
perform amplitude apodization on the sub-echo signal corresponding to the scan depth range of 12.5 cm-17.5 cm with the cosine window function and the rectangular window function; and
perform amplitude apodization on the sub-echo signal corresponding to the scan depth range of 17.5 cm-20 cm with the cosine window function and the rectangular window function In some implementations, the second predetermined number may be any integer from 8 to 12.

In some implementations, the processing unit 402 may be configured to:
assign two sets of weighting coefficients to each unit echo signal, with the two sets of weighting coefficients being a set of weighting coefficients in ascending order of value and a set of weighting coefficients in descending order of value respectively;

perform amplitude apodization on each unit echo signal with two corresponding predetermined window functions to obtain two sets of processing results;

weight the two sets of processing results with the two sets of weighting coefficients respectively to obtain two sets of weighted processing results; and obtain the processed unit echo signal according to the two sets of weighted processing results.

In some implementations, the processing unit 402 may be configured to:

segment the sub-echo signal into 11 unit echo signals according to scan depths. The sub-echo signal is the sub-echo signal corresponding to the scan depth range of 2.5 cm-7.5 cm, 7.5 cm-12.5 cm or 12.5 cm-17.5 cm, a difference between a maximum scan depth and a minimum scan depth of the scan depth range of each of the first unit echo signal and the last unit echo signal among the 11 unit echo signals is 0.25 cm, and each of the scan depth ranges of the other 9 unit echo signals (i.e., the second unit echo signal to the tenth unit echo signal) among the 11 unit echo signals has a span of 0.5 cm.

In some implementations, the weighting coefficients in ascending order of value are integers from 0 to 10, and the weighting coefficients in descending order of value are integers from 10 to 0.

In some implementations, the processing unit 402 may be configured to:

perform amplitude apodization on the sub-echo signal corresponding to the scan depth range of 0-2.5 cm with the Blackman window function to obtain a processing result, and then multiply the processing result by a weighting coefficient of 10; and perform amplitude apodization on the sub-echo signal corresponding to the scan depth range of 17.5 cm-20 cm with the rectangular window function to obtain a processing result, and then multiply the processing result by a weighting coefficient of 10.

For convenience of description, in the description of the above device, the device is divided by functions into various modules which are described separately. It should be understood that the function of each module may be implemented in the same or multiple software and/or hardware when the one or more embodiments of the present disclosure are implemented.

The device described in the above embodiments is used for implementing the corresponding method described in the foregoing embodiments, and has the beneficial effects of the corresponding method, which are not repeated here.

The present disclosure further provides a non-transitory computer-readable storage medium having computer instructions stored therein. When executed by a processor, the computer instructions causes a computer to perform the method described herein.

The computer-readable medium of the present disclosure includes permanent/non-permanent media and removable/non-removable media, and can achieve information storage with any method or technique. The information may be computer-readable instructions, data structures, modules of a program, or other data. Examples of a storage medium of a computer include, but are not limited to, a Phase-change Memory (PRAM), a Static Random Access Memory (SRAM), a Dynamic Random Access Memory (DRAM), other types of Random Access Memories (RAMs), a Read-Only Memory (ROM), an Electrically Erasable Programmable Read-Only Memory (EEPROM), a flash memory or other memory technology, a Compact Disc Read-Only Memory (CD-ROM), a Digital Versatile Disk (DVD) or other optical memories, a magnetic cassette, a magnetic tape, a magnetic disk or other magnetic storage devices, or any other non-transmission medium, which can be used to store information that can be accessed by a computing device.

The specific embodiments of the present disclosure are described above. The other embodiments fall within the scope of the appended claims. In some cases, the operations or steps described in the claims may be performed in an order different from that described in the embodiments and can still produce desirable results. In addition, the processes illustrated by the drawings do not necessarily indicate that the desirable results can be produced only by performing in a particular or continuous order as shown in the drawings. In some implementations, multitasking and parallel processing are feasible or may be advantageous.

It should be understood by those of ordinary skill in the art that the above discussion of any embodiment is merely illustrative, and is not intended to indicate that the scope of the present disclosure (including that of the claims) is limited to those embodiments; and the above embodiments or the technical features in the different embodiments can be combined with one another based on the idea of the present disclosure, the steps may be performed in any order, various other changes may be made in different aspects of the above one or more embodiments of the present disclosure, but those changes are not provided in detail herein for simplicity.

In addition, for simplifying the description and the discussion and not obscuring the one or more embodiments of the present disclosure, well-known power/ground connections to Integrated Circuit (IC) chips and other components may be shown in the accompanying drawings or not. Moreover, the device may be illustrated by block diagrams, so as to avoid obscuring the one or more embodiments of the present disclosure; and the use of the block diagrams also takes account of a fact that the details of the implementations of the device illustrated by the block diagrams are highly dependent upon the platform where the one or more embodiments of the present disclosure are to be implemented (that is, those details should be completely within the scope of understanding of those of ordinary skill in the art). Under the condition that the exemplary embodiments of the present disclosure are described in detail by elaborating details (for example, a circuit), it should be apparent to those of ordinary skill in the art that the one or more embodiments of the present disclosure can be implemented without those details or when those details change. Therefore, the description should be regarded as being illustrative instead of restrictive.

With the present disclosure described in conjunction with the specific embodiments thereof, many alternatives, modifications and variations made according to the above description will be apparent to those of ordinary skill in the art. For example, other memory architectures (e.g., a Dynamic RAM (DRAM)) may adopt the embodiments discussed.

The one or more embodiments of the present disclosure are intended to cover all of the alternatives, modifications and variations which fall within the broad scope of the appended claims. Therefore, any omission, modification, equivalent replacement and improvement made without departing from the essence or principle of the present disclosure should be included in the scope of the present disclosure.

What is claimed is:

1. An ultrasonic imaging method, comprising:
acquiring an ultrasonic echo signal;
segmenting the ultrasonic echo signal into five sub-echo signals according to scan depths, with scan depth ranges corresponding to the sub-echo signals being 0-2.5 cm, 2.5 cm-7.5 cm, 7.5 cm-12.5 cm, 12.5 cm-17.5 cm and 17.5 cm-20 cm respectively;
performing amplitude apodization on each of the sub-echo signals with a predetermined window function to obtain processed sub-echo signals; and
completing ultrasonic imaging according to the processed sub-echo signals,
wherein, at least one of the sub-echo signals is subjected to follow processing:
segmenting the at least one of the sub-echo signals into a second predetermined number of unit echo signals according to the scan depths, and assigning weighting coefficients to each of the unit echo signals;
performing amplitude apodization on each of the unit echo signals with the predetermined window function corresponding to the at least one of the sub-echo signals, and weighting the unit echo signals with the weighting coefficients corresponding to the unit echo signals to obtain processed unit echo signals; and
forming the processed sub-echo signal from the second predetermined number of processed unit echo signals.

2. The method of claim 1, further comprising:
outputting an ultrasonic imaging result.

3. The method of claim 2, wherein the predetermined window function comprises at least one of a Blackman window function, a Hanning window function, a cosine window function and a rectangular window function.

4. The method of claim 1, wherein the predetermined window function comprises at least one of a Blackman window function, a Hanning window function, a cosine window function and a rectangular window function.

5. The method of claim 4, wherein,
the Blackman window function corresponds to the scan depth of 2.5 cm, the Hanning window function corresponds to the scan depth of 7.5 cm, the cosine window function corresponds to the scan depth of 12.5 cm, and the rectangular window function corresponds to the scan depth of 17.5 cm; and
performing amplitude apodization on each of the sub-echo signals with the predetermined window function comprises:
performing amplitude apodization on the sub-echo signal having the scan depth range of 0-2.5 cm with the Blackman window function;
performing amplitude apodization on the sub-echo signal having the scan depth range of 2.5 cm-7.5 cm with the Blackman window function and the Hanning window function;
performing amplitude apodization on the sub-echo signal having the scan depth range of 7.5 cm-12.5 cm with the Hanning window function and the cosine window function;
performing amplitude apodization on the sub-echo signal having the scan depth range of 12.5 cm-17.5 cm with the cosine window function and the rectangular window function; and
performing amplitude apodization on the sub-echo signal having the scan depth range of 17.5 cm-20 cm with the rectangular window function.

6. The method of claim 1, wherein the second predetermined number is any integer from 8 to 12.

7. The method of claim 6, wherein assigning the weighting coefficients to each of the unit echo signals comprises:
assigning two sets of weighting coefficients to the unit echo signals, with the two sets of weighting coefficients being a set of weighting coefficients in ascending order of value and a set of weighting coefficients in descending order of value respectively; and
performing amplitude apodization on each of the unit echo signals with the predetermined window function corresponding to the at least one of the sub-echo signals, and weighting the unit echo signals with the weighting coefficients corresponding to the unit echo signals to obtain the processed unit echo signals comprises:
performing amplitude apodization on each of the unit echo signals with two corresponding predetermined window functions to obtain two sets of processing results;
weighting the two sets of processing results with the two sets of weighting coefficients respectively to obtain two sets of weighted processing results; and
obtaining the processed unit echo signal according to the two sets of weighted processing results.

8. The method of claim 7, wherein segmenting the at least one of the sub-echo signals into the second predetermined number of unit echo signals according to the scan depths comprises:
segmenting each of the least one of the sub-echo signals into 11 unit echo signals according to the scan depths; wherein the sub-echo signal is a sub-echo signal corresponding to the scan depth range of 2.5 cm-7.5 cm, 7.5 cm-12.5 cm or 12.5 cm-17.5 cm, a difference between a maximum scan depth and a minimum scan depth of the scan depth range of each of the first unit echo signal and the last unit echo signal among the 11 unit echo signals is 0.25 cm, and each of the scan depth ranges of the second unit echo signal to the tenth unit echo signal among the 11 unit echo signals has a span of 0.5 cm; and
the weighting coefficients in ascending order of value are integers from 0 to 10, and the weighting coefficients in descending order of value are integers from 10 to 0.

9. The method of claim 8, further comprising:
performing amplitude apodization on the sub-echo signal having the scan depth range of 0-2.5 cm with the Blackman window function to obtain a processing result, and then multiplying the processing result by a weighting coefficient of 10; and
performing amplitude apodization on the sub-echo signal having the scan depth range of 17.5 cm-20 cm with the rectangular window function to obtain a processing result, and then multiplying the processing result by a weighting coefficient of 10.

10. A non-transitory computer-readable storage medium having computer instructions stored therein, wherein, the computer instructions cause, when executed by a processor, a computer to perform the method of claim 1.

11. An ultrasonic imaging device, comprising:
an acquisition unit configured to acquire an ultrasonic echo signal; and
a processing unit configured to:
segment the ultrasonic echo signal into five sub-echo signals according to scan depths, with scan depth ranges corresponding to the sub-echo signals being 0-2.5 cm, 2.5 cm-7.5 cm, 7.5 cm-12.5 cm, 12.5 cm-17.5 cm and 17.5 cm-20 cm respectively;

perform amplitude apodization on each of the sub-echo signals with a predetermined window function to obtain processed sub-echo signals; and complete ultrasonic imaging according to the processed sub-echo signals, wherein, the processing unit is further configured to:

segment at least one of the sub-echo signals into a second predetermined number of unit echo signals according to scan depths, and assign weighting coefficients to each of the unit echo signals;

perform amplitude apodization on each of the unit echo signals with the predetermined window function corresponding to the at least one of the sub-echo signals, and weight the unit echo signals with the weighting coefficients corresponding to the unit echo signals to obtain processed unit echo signals; and form the processed sub-echo signal from the second predetermined number of processed unit echo signals.

12. The device of claim 11, further comprising:
an output unit configured to output an ultrasonic imaging result.

13. The device of claim 11, wherein the predetermined window function comprises at least one of a Blackman window function, a Hanning window function, a cosine window function and a rectangular window function.

14. The device of claim 13, wherein,
the Blackman window function corresponds to the scan depth of 2.5 cm, the Hanning window function corresponds to the scan depth of 7.5 cm, the cosine window function corresponds to the scan depth of 12.5 cm, and the rectangular window function corresponds to the scan depth of 17.5 cm; and the processing unit is further configured to:

perform amplitude apodization on the sub-echo signal having the scan depth range of 0-2.5 cm with the Blackman window function;

perform amplitude apodization on the sub-echo signal having the scan depth range of 2.5 cm-7.5 cm with the Blackman window function and the Hanning window function;

perform amplitude apodization on the sub-echo signal having the scan depth range of 7.5 cm-12.5 cm with the Hanning window function and the cosine window function;

perform amplitude apodization on the sub-echo signal having the scan depth range of 12.5 cm-17.5 cm with the cosine window function and the rectangular window function; and perform amplitude apodization on the sub-echo signal having the scan depth range of 17.5 cm-20 cm with the rectangular window function.

15. The device of claim 14, wherein the processing unit is further configured to:

assign two sets of weighting coefficients to the unit echo signals, with the two sets of weighting coefficients being a set of weighting coefficients in ascending order of value and a set of weighting coefficients in descending order of value respectively;

perform amplitude apodization on each of the unit echo signals with two corresponding predetermined window functions to obtain two sets of processing results;

weight the two sets of processing results with the two sets of weighting coefficients to obtain two sets of weighted processing results; and obtain the processed unit echo signal according to the two sets of weighted processing results.

16. The device of claim 15, wherein the processing unit is further configured to:

segment each of the at least one sub-echo signal into 11 unit echo signals according to the scan depths; wherein the sub-echo signal is the sub-echo signal corresponding to the scan depth range of 2.5 cm-7.5 cm, 7.5 cm-12.5 cm or 12.5 cm-17.5 cm, a difference between a maximum scan depth and a minimum scan depth of the scan depth range of each of the first unit echo signal and the last unit echo signal among the 11 unit echo signals is 0.25 cm, and each of the scan depth ranges of the second unit echo signal to the tenth unit echo signal among the 11 unit echo signals has a span of 0.5 cm; and the weighting coefficients in ascending order of value are integers from 0 to 10, and the weighting coefficients in descending order of value are integers from 10 to 0.

17. The device of claim 15, wherein the processing unit is further configured to:

perform amplitude apodization on the sub-echo signal having the scan depth range of 0-2.5 cm with the Blackman window function to obtain a processing result, and then multiply the processing result by a weighting coefficient of 10; and perform amplitude apodization on the sub-echo signal having the scan depth range of 17.5 cm-20 cm with the rectangular window function to obtain a processing result, and then multiply the processing result by a weighting coefficient of 10.

* * * * *

UNITED STATES PATENT AND TRADEMARK OFFICE
CERTIFICATE OF CORRECTION

PATENT NO. : 12,161,508 B2
APPLICATION NO. : 17/626657
DATED : December 10, 2024
INVENTOR(S) : Jijing Huang et al.

Page 1 of 1

It is certified that error appears in the above-identified patent and that said Letters Patent is hereby corrected as shown below:

On the Title Page

Item (30) the Foreign Application Priority Data reading -202010177896.3- should read --2020101778966--

Signed and Sealed this
First Day of July, 2025

Coke Morgan Stewart
*Acting Director of the United States Patent and Trademark Office*